US012599705B2

(12) United States Patent
Nakai et al.

(10) Patent No.: US 12,599,705 B2
(45) Date of Patent: Apr. 14, 2026

(54) FLEXIBLE TUBE FOR ENDOSCOPE, ENDOSCOPIC MEDICAL DEVICE, METHOD FOR PRODUCING COVERING MATERIAL CONSTITUTING FLEXIBLE TUBE FOR ENDOSCOPE, AND METHOD FOR PRODUCING FLEXIBLE TUBE FOR ENDOSCOPE

(71) Applicant: FUJIFILM Corporation, Tokyo (JP)

(72) Inventors: Yoshihiro Nakai, Kanagawa (JP); Kazushi Furukawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 519 days.

(21) Appl. No.: 18/147,277

(22) Filed: Dec. 28, 2022

(65) Prior Publication Data

US 2023/0133400 A1 May 4, 2023

Related U.S. Application Data

(63) Continuation of application No. PCT/JP2021/024359, filed on Jun. 28, 2021.

(30) Foreign Application Priority Data

Jun. 29, 2020 (JP) ................................. 2020-111753

(51) Int. Cl.
*A61L 29/08* (2006.01)

(52) U.S. Cl.
CPC ......... *A61L 29/085* (2013.01); *A61L 2420/02* (2013.01)

(58) Field of Classification Search
None
See application file for complete search history.

(56) References Cited

U.S. PATENT DOCUMENTS

| | | |
|---|---|---|
| 2001/0029317 A1 | 10/2001 | Hayakawa |
| 2009/0198021 A1 | 8/2009 | Ogura et al. |
| 2010/0280319 A1 | 11/2010 | Ogura et al. |
| 2016/0088998 A1 | 3/2016 | Nagai et al. |
| 2020/0100652 A1 | 4/2020 | Yoshitani et al. |

(Continued)

FOREIGN PATENT DOCUMENTS

| | | | |
|---|---|---|---|
| CN | 105455764 A | | 4/2016 |
| JP | H1192638 | * | 4/1999 |
| JP | 2001-275936 A | | 10/2001 |

(Continued)

OTHER PUBLICATIONS

International Search Report dated Sep. 14, 2021 in Application No. PCT/JP2021/024359.

(Continued)

*Primary Examiner* — Yan Lan
(74) *Attorney, Agent, or Firm* — Sughrue Mion, PLLC

(57) ABSTRACT

Provided are a flexible tube for an endoscope, the flexible tube having a flexible-tube base that is flexible and tubular and a polyester elastomer layer that covers the flexible-tube base and has a naphthalene structure in a soft segment, an endoscopic medical device having the flexible tube for an endoscope, a method for producing a covering material constituting the flexible tube for an endoscope, and a method for producing the flexible tube for an endoscope.

11 Claims, 2 Drawing Sheets

(56) References Cited

U.S. PATENT DOCUMENTS

| | | | |
|---|---|---|---|
| 2020/0345327 | A1 | 11/2020 | Nakai |
| 2020/0405918 | A1 | 12/2020 | Nakai et al. |

FOREIGN PATENT DOCUMENTS

| | | | | |
|---|---|---|---|---|
| JP | 2004-141487 | A | | 5/2004 |
| JP | 2004141487 | | * | 5/2004 |
| JP | 2009-183467 | A | | 8/2009 |
| WO | 2019/012826 | A1 | | 1/2019 |
| WO | 2019/151135 | A1 | | 8/2019 |
| WO | 2019/189035 | A1 | | 10/2019 |

OTHER PUBLICATIONS

Written Opinion of the International Searching Authority dated Sep. 14, 2021 in Application No. PCT/JP2021/024359.
International Preliminary Report on Patentability dated Dec. 13, 2022 with a Translation of the Written Opinion of the International Searching Authority in Application No. PCT/JP2021/024359.
Communication dated Jun. 28, 2025 in Chinese Application No. 202180043565.6.

* cited by examiner

FLEXIBLE TUBE FOR ENDOSCOPE, ENDOSCOPIC MEDICAL DEVICE, METHOD FOR PRODUCING COVERING MATERIAL CONSTITUTING FLEXIBLE TUBE FOR ENDOSCOPE, AND METHOD FOR PRODUCING FLEXIBLE TUBE FOR ENDOSCOPE

CROSS-REFERENCE TO RELATED APPLICATIONS

This application is a Continuation of PCT International Application No. PCT/JP2021/024359 filed on Jun. 28, 2021, which claims priority under 35 U.S.C. § 119 (a) to Japanese Patent Application No. 2020-111753 filed in Japan on Jun. 29, 2020. Each of the above applications is hereby expressly incorporated by reference, in its entirety, into the present application.

BACKGROUND OF THE INVENTION

1. Field of the Invention

The present invention relates to a flexible tube for an endoscope, an endoscopic medical device, a method for producing a covering material constituting a flexible tube for an endoscope, and a method for producing a flexible tube for an endoscope.

2. Description of the Related Art

Endoscopes are medical devices for examination of a patient's body cavity, digestive tract, esophagus, etc. Since endoscopes are used as inserted in the body, those which do not damage organs or cause pain and/or discomfort to a patient are desired. To meet this need, a spiral tube formed by spirally winding a soft, bendable metal strip is adopted as a flexible tube constituting an insertion section of an endoscope. Furthermore, the periphery of the spiral tube is covered with a flexible resin so that the spiral tube does not cause stimulation or damage to the inner surfaces of the esophagus, digestive tract, body cavity, etc.

An endoscope for examining the interior of the human body is repeatedly used. Thus, a flexible tube constituting an insertion section of the endoscope needs to be washed and disinfected with a chemical after each use. In particular, when the endoscope is inserted into a highly susceptible region, such as a bronchus, cleanliness at the level of sterilization higher than disinfection is required. Accordingly, flexible tubes for endoscopes have been required to have high durability sufficient to withstand repeated sterilization treatment.

For example, WO2019/189035A discloses that when a thermoplastic resin having a 10% tensile strength of 10 MPa or more is used as a constituent material of a resin layer covering a flexible-tube base, and a hindered amine compound with a molecular weight of 500 or more is mixed with the resin, deterioration of the resin layer is less likely to occur even if hydrogen peroxide plasma treatment is repeated or hydrogen peroxide gas treatment is repeated.

JP2004-141487A discloses a flexible tube for an endoscope, the flexible tube including a flexible-tube material and an outer skin covering a surface of the flexible-tube material. In the flexible tube, polybutylene naphthalate is used as a hard segment of a polyester elastomer constituting the outer skin, whereby deterioration of the outer skin due to a washing solution or an antiseptic solution is suppressed.

JP2009-183467A discloses that a flexible tube for an endoscope, the flexible tube being covered with an outer skin formed of an elastomer molded body for an endoscope obtained by cross-linking two or more thermoplastic polyester elastomers, is resistant to various chemicals and less likely to undergo outer skin deterioration.

SUMMARY OF THE INVENTION

Regarding the sterilization durability of a flexible tube for an endoscope, sterilization treatment using ozone water obtained by dissolving a trace amount of ozone ($O_3$) in water has recently been performed. However, such ozone water generates strong active species such as hydroxyl radicals, whose oxidizing power is stronger than that of hydrogen peroxide gas. Therefore, fluorine-based resins are only known as organic materials that can withstand sterilization treatment with ozone water.

In addition, a flexible tube used in a thin tube such as a bronchus is required to have a sufficiently small diameter. As the flexible tube diameter becomes smaller, the flexible tube operability from an endoscope operation section decreases. For example, when a flexible tube is inserted into a bronchus, the flexible tube is inserted in the bronchus in a bent state along a branching structure of the bronchus. When an endoscope operation section at hand is pushed or rotated in this state, the physical change of the operation section may be insufficiently transmitted to the distal end portion of the endoscope flexible tube inserted in the body. In this case, it may be difficult to perform an appropriate clinical examination or clinical treatment.

In view of the foregoing, an object of the present invention is to provide a flexible tube for an endoscope and an endoscopic medical device using the flexible tube. The flexible tube can sufficiently and efficiently transmit the motion of an endoscope operation section to the distal end portion of the flexible tube and exhibits high sterilization durability against powerful sterilization treatment with, for example, ozone water. Another object of the present invention is to provide a method for producing a covering material constituting the flexible tube for an endoscope and a method for producing the flexible tube for an endoscope.

In view of the foregoing problems, the present inventors have conducted intensive studies and found that the foregoing problems can be solved by using, as a constituent material of an outer skin constituting a flexible tube for an endoscope, a polyester elastomer in which a naphthalene structure is incorporated in a soft segment, thereby completing the present invention.

The above objects have been achieved by the following means.

<1>

A flexible tube for an endoscope has a flexible-tube base that is flexible and tubular and a polyester elastomer layer covering the flexible-tube base.

The polyester elastomer has a naphthalene structure in a soft segment.

<2>

In the flexible tube for an endoscope according to <1>, a proportion of a naphthalenedicarboxylic acid component in a whole dicarboxylic acid component constituting the soft segment is 2 to 100 mol %.

<3>

In the flexible tube for an endoscope according to <1> or <2>, the polyester elastomer has a naphthalene structure in a hard segment.

3

<4>

In the flexible tube for an endoscope according to <3>, the hard segment has a naphthalenedicarboxylic acid component and a phthalic acid component.

<5>

In the flexible tube for an endoscope according to <4>, at least a part of the phthalic acid component is an isophthalic acid component.

<6>

In the flexible tube for an endoscope according to any one of <3> to <5>, a proportion of a naphthalenedicarboxylic acid component in a whole dicarboxylic acid component constituting the hard segment is 5 to 90 mol %.

<7>

In the flexible tube for an endoscope according to any one of <4> to <6>, a proportion of the phthalic acid component in a whole dicarboxylic acid component constituting the hard segment is 10 to 95 mol %.

<8>

In the flexible tube for an endoscope according to any one of <5> to <7>, a proportion of the isophthalic acid component in a whole dicarboxylic acid component constituting the hard segment is 10 to 40 mol %.

<9>

In the flexible tube for an endoscope according to any one of <1> to <8>, the soft segment has a number-average molecular weight of 10,000 or more and less than 21,000.

<10>

An endoscopic medical device has the flexible tube for an endoscope according to any one of <1> to <9>.

<11>

A method for producing a covering material constituting a flexible tube for an endoscope includes:

a step of subjecting a polyalkylene glycol with a number-average molecular weight of 1,000 or more as a diol compound and at least naphthalene dicarboxylic acid as a dicarboxylic acid compound to an esterification reaction to obtain a polyester compound; and a step of subjecting the polyester compound, a diol compound with a molecular weight of 500 or less, and a dicarboxylic acid compound to an esterification reaction to obtain a polyester elastomer having the polyester compound as a soft segment.

<12>

A method for producing a flexible tube for an endoscope includes covering a flexible-tube base with a covering material obtained by the method according to <11>.

The flexible tube for an endoscope according to the present invention can sufficiently and efficiently transmit the motion of an endoscope operation section to the distal end portion of the flexible tube and exhibits high sterilization durability against powerful sterilization treatment with, for example, ozone water. The endoscopic medical device according to the present invention is a device equipped with a flexible tube for an endoscope having the above-described excellent characteristics. According to the method for producing a covering material constituting a flexible tube for an endoscope according to the present invention, a covering material that exhibits the above-described characteristics can be provided. According to the method for producing a flexible tube for an endoscope according to the present invention, the flexible tube for an endoscope according to the present invention having the above-described characteristics can be provided.

4

Figure 2:
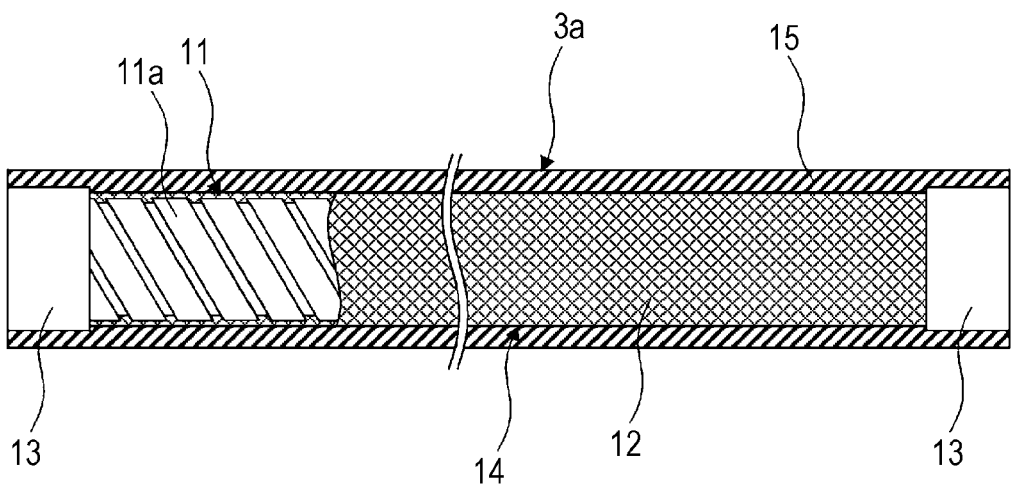

FIG. 2 is a partial sectional view showing a schematic configuration of a flexible tube for an endoscope.

DESCRIPTION OF THE PREFERRED
EMBODIMENTS

Figure 1:
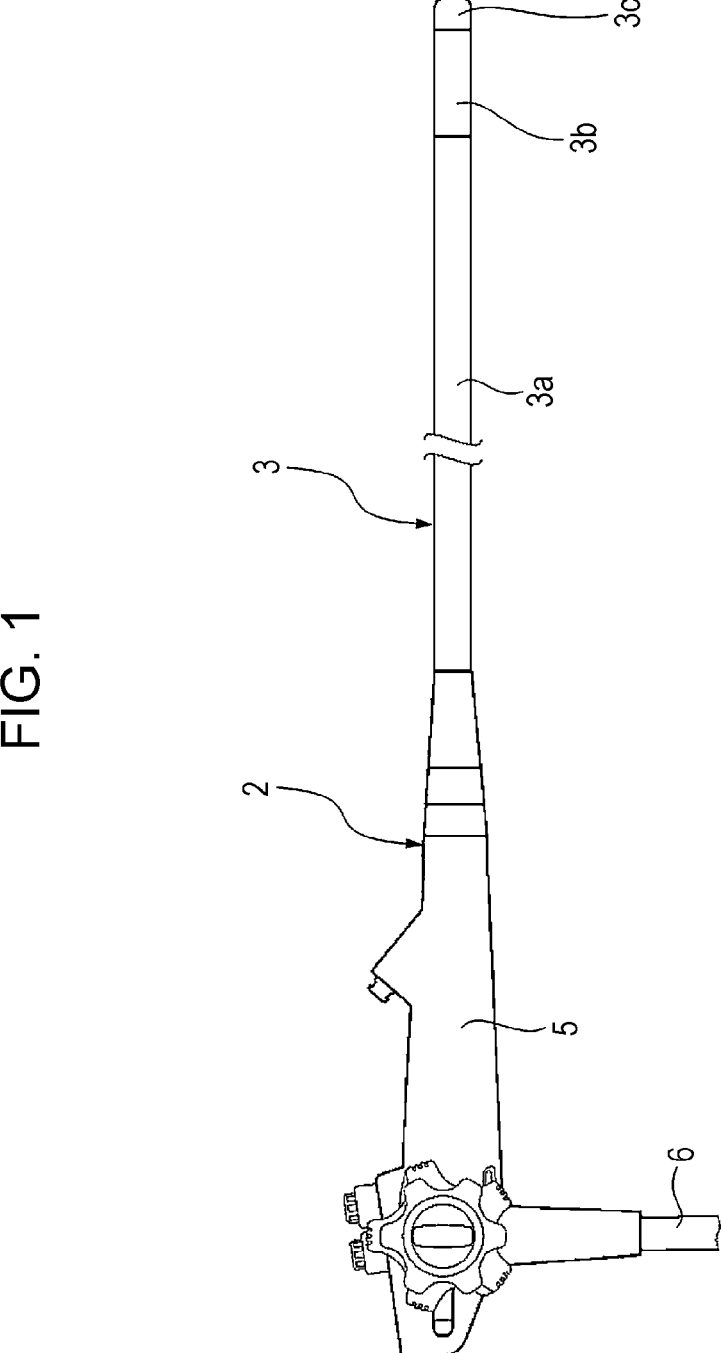
FIG. 1 is an external view showing a configuration of an electronic endoscope.

An endoscopic medical device according a preferred embodiment of the present invention will be described in the context of an electronic endoscope. An electronic endoscope is incorporated with a flexible tube for an endoscope (hereinafter a flexible tube for an endoscope may be referred to simply as a "flexible tube") and is used as a medical device for, for example, examining the inside of a body with the flexible tube inserted in the body cavity, digestive tract, esophagus, or the like. In the example shown in FIG. 1, an electronic endoscope 2 includes an insertion section 3 to be inserted into a body, a main-body operation section 5 connected to the proximal end portion of the insertion section 3, and a universal cord 6 to be connected to a processor device or a light source device. The insertion section 3 is composed of a flexible tube 3a connected to the main-body operation section 5, an angle portion 3b connected to the flexible tube 3a, and a tip portion 3c connected to the distal end of the angle portion 3b and containing an image pick-up device (not shown) for imaging the inside of the body. The flexible tube 3a, which occupies most of the length of the insertion section 3, is flexible over substantially the entire length thereof. In particular, a portion to be inserted inside the esophagus, digestive tract, body cavity, or the like has a more flexible structure.

Flexible Tube

As shown in FIG. 2, the flexible tube 3a (flexible tube for an endoscope) has a flexible-tube base 14 and a polyester elastomer layer 15 covering the outer peripheral surface of the flexible-tube base 14. The flexible-tube base 14 includes a spiral tube 11 disposed on the innermost side and formed by spirally winding a metal strip 11a, a tubular mesh 12 covering the spiral tube 11 and formed by braiding metal wires, and caps 13 fitted to both ends. Although the spiral tube 11 is shown as a single layer, it may be composed of two layers coaxially stacked on top of each other. To clearly illustrate the layer structure, the polyester elastomer layer 15 is shown as being thick relative to the diameter of the flexible-tube base 14.

In this embodiment, the polyester elastomer layer 15 is formed so as to have a substantially uniform thickness in the longitudinal direction (axial direction) of the flexible-tube base 14. The thickness of the polyester elastomer layer 15 is, for example, 0.1 to 0.6 mm. The outer diameter D of the flexible tube 3a is, for example, 2.0 to 10.0 mm, preferably 3.0 to 8.0 mm. The outer diameter of the flexible-tube base 14 is, for example, 1.6 to 9.6 mm, preferably 2.2 to 7.8 mm. In the case of a small-sized endoscope whose insertion section 3 is inserted into a bronchus, the thickness of the polyester elastomer layer 15 is preferably 0.1 to 0.3 mm. In this case, the outer diameter D of the flexible tube 3a is preferably 3.0 to 5.0 mm, and the outer diameter of the flexible-tube base 14 is preferably 2.4 to 4.8 mm.

The flexible tube according to the present invention has a flexible-tube base that is flexible and tubular and the polyester elastomer layer 15 covering the flexible-tube base.

The polyester elastomer layer 15 may be composed of a single layer or a plurality of layers having different compositions (a plurality of layers whose compositional ratios of a constituent dicarboxylic acid component or diol component are different from each other). The polyester elastomer layer 15 is preferably composed of a single layer.

The flexible tube according to the present invention may have a top coat layer on the outside of the polyester elastomer layer 15. For the configuration of the topcoat layer, for example, reference can be made to the description in JP2015-16261A.

Polyester Elastomer

The polyester elastomer layer 15 is a layer containing, as a main constituent material, a polyester elastomer having a specific structure described later.

The polyester elastomer constituting the polyester elastomer layer 15 (hereinafter referred to as the "polyester elastomer used in the present invention") is a block copolymer constituted by a soft segment composed of a polyester chain having a naphthalene structure and a hard segment composed of a crystalline polyester structure.

The polyester constituting the soft segment preferably includes a naphthalenedicarboxylic acid component as a dicarboxylic acid component and a polymer diol component as a diol component.

The proportion of the naphthalenedicarboxylic acid component in the whole dicarboxylic acid component (100 mol %) constituting the soft segment is preferably 2 to 100 mol %, more preferably 4 to 100 mol %, still more preferably 10 to 100 mol %, particularly preferably 20 to 100 mol %, more particularly preferably 50 to 100 mol %, most preferably 60 to 100 mol %. It is also preferable that the dicarboxylic acid component constituting the soft segment consists only of the naphthalenedicarboxylic acid component.

In the present invention, examples of the naphthalenedicarboxylic acid component include a 2,6-naphthalenedicarboxylic acid component.

When the soft segment includes, in addition to the naphthalenedicarboxylic acid component, a dicarboxylic acid component other than the naphthalenedicarboxylic acid component, the dicarboxylic acid component is not particularly limited, and a wide variety of dicarboxylic acid components that can be commonly used as dicarboxylic acid components of polyester compounds can be used. The dicarboxylic acid component may be a component derived from, for example, phthalic acid, oxalic acid, succinic acid, adipic acid, sebacic acid, azelaic acid, dodecanedioic acid, maleic acid, fumaric acid, itaconic acid, citraconic acid, mesaconic acid, and/or cyclohexanedicarboxylic acid. That is, the soft segment may have a constituent component derived from one or two or more of these exemplified dicarboxylic acids.

In particular, the soft segment preferably has a phthalic acid component, more preferably has at least one of a terephthalic acid component or an isophthalic acid component, and still more preferably has a terephthalic acid component.

The polymer diol component constituting the soft segment has a number-average molecular weight of preferably 1,000 or more, more preferably 1,200 or more, still more preferably 1,500 or more. The number-average molecular weight of the polymer diol component is preferably 10,000 or less, more preferably 6,000 or less, also preferably 4,000 or less. The soft segment may have a diol component (low-molecular-weight diol compound) other than the polymer diol component as long as the effects of the present invention are not impaired, but the diol component of the soft segment is usually composed of the polymer diol component.

Preferred examples of the polymer diol component include polyalkylene glycol-derived components such as polyethylene glycol, polypropylene glycol, and polytetramethylene oxide glycol (polytetramethylene ether glycol). In the present invention, polyalkylene glycol is a compound represented by HO—$[(CH_2)_mO]_n$—H. Here, m is preferably 1 to 12, more preferably 2 to 10, still more preferably 2 to 8, particularly preferably 2 to 6. n is preferably 5 to 100, more preferably 10 to 50.

The molecular weight of the soft segment can be appropriately set within a range that does not impair the effects of the present invention. For example, the number-average molecular weight can be 5,000 or more, and is preferably 10,000 or more and less than 21,000, more preferably 10,000 to 20,000, still more preferably 11,000 to 18,000, particularly preferably 11,000 to 16,000.

In the present invention, the number-average molecular weight of the soft segment and the weight-average molecular weight of the polymer are determined (in terms of standard polystyrene) by gel permeation chromatography using chloroform as an eluant and G3000HXL+G2000HXL (trade names, manufactured by Tosoh Corporation) as columns under the following conditions: 23° C.; flow rate, 1 mL/min; RI detection.

The soft segment constitutes preferably 10 to 90 mass %, more preferably 20 to 80 mass %, and still more preferably 25 to 75 mass % of the polyester elastomer.

The structure of the hard segment is not particularly limited as long as it functions as a hard segment of the polyester elastomer. From the viewpoint of improving the operability of the flexible tube, the hard segment preferably has a naphthalene structure.

The hard segment is composed of a dicarboxylic acid component and a diol component. The hard segment may have a hydroxycarboxylic acid component.

The dicarboxylic acid component constituting the hard segment is not particularly limited, and a wide variety of dicarboxylic acid components commonly used for hard segments of polyester elastomers can be used. The molecular weight of the dicarboxylic acid component constituting the hard segment is preferably 400 or less. The dicarboxylic acid component may be a component derived from, for example, phthalic acid, naphthalenedicarboxylic acid, oxalic acid, succinic acid, adipic acid, sebacic acid, azelaic acid, dodecanedioic acid, dimer acid, maleic acid, fumaric acid, itaconic acid, citraconic acid, mesaconic acid, and/or cyclohexanedicarboxylic acid. That is, the hard segment may have a constituent component derived from one or two or more of these exemplified dicarboxylic acid compounds. The dicarboxylic acid component constituting the hard segment preferably includes an aromatic dicarboxylic acid component (a dicarboxylic acid component having an aromatic ring), and 50 mass % or more (preferably 70 mass % or more, more preferably 80 mass % or more, still more preferably 90 mass % or more) of the dicarboxylic acid component constituting the hard segment is preferably constituted by the aromatic dicarboxylic acid component. It is also preferable that the dicarboxylic acid component constituting the hard segment consists only of the aromatic dicarboxylic acid component.

In particular, the hard segment preferably has at least one of a phthalic acid component or a naphthalenedicarboxylic acid component. When the hard segment has a phthalic acid component, the hard segment preferably has at least one of terephthalic acid or isophthalic acid. The dicarboxylic acid component constituting the hard segment more preferably has a naphthalenedicarboxylic acid component and a phthalic acid component (at least one of a terephthalic acid component or an isophthalic acid component), and from the viewpoint of the operability of the flexible tube, it is more preferable that at least a part of the phthalic acid component is an isophthalic acid component. That is, from the viewpoint of the operability of the flexible tube, it is still more preferable that the hard segment has a naphthalenedicarboxylic acid component and an isophthalic acid component.

When the hard segment has a naphthalenedicarboxylic acid component, the naphthalenedicarboxylic acid component may constitute the whole dicarboxylic acid component constituting the hard segment. The proportion of the naphthalenedicarboxylic acid component in the whole dicarboxylic acid component (100 mol %) constituting the hard segment is preferably 5 to 90 mol %, more preferably 10 to 80 mol %.

When the hard segment has a phthalic acid component, the phthalic acid component may constitute the whole dicarboxylic acid component constituting the hard segment. The proportion of the phthalic acid component in the whole dicarboxylic acid component constituting the hard segment is preferably 10 to 95 mol %, more preferably 20 to 90 mol %. In the hard segment, the proportion of isophthalic acid in the whole dicarboxylic acid component is preferably 10 to 40 mol %, more preferably 15 to 30 mol %.

The diol component constituting the hard segment is not particularly limited, and a wide variety of diol components commonly used for hard segments of polyester elastomers can be used. The molecular weight of the diol component constituting the hard segment is preferably 500 or less. The diol component may be a component derived from, for example, ethylene glycol, diethylene glycol, 1,3-propanediol, 1,4-butanediol, neopentyl glycol, 1,6-hexanediol, cyclohexanedimethanol, triethylene glycol, bisphenol A, and/or bisphenol S. That is, the hard segment may have a constituent component derived from one or two or more of these exemplified diol compounds.

In particular, the hard segment preferably has at least one of an ethylene glycol component, a diethylene glycol component, a 1,3-propanediol component, or a 1,4-butanediol component, more preferably has at least one of an ethylene glycol component, a 1,3-propanediol components, or a 1,4-butanediol component, and still more preferably has a 1,4-butanediol component.

When the hard segment has a hydroxycarboxylic acid component, it may be a component derived from 6-hydroxycaproic acid, lactic acid, 4-hydroxybenzoic acid, or the like.

The hard segment may be a homopolymer or copolymer composed of the above components.

The molecular weight of the polyester elastomer used in the present invention is not particularly limited and can be, for example, 10,000 to 300,000 in terms of weight-average molecular weight, and is typically 20,000 to 100,000 in terms of weight-average molecular weight.

The polyester elastomer used in the present invention can be obtained by forming a polyester chain constituting the soft segment, and then mixing the polyester chain with a dicarboxylic acid compound, a diol compound, and the like serving as raw materials of the hard segment to cause a polycondensation reaction. For example, the polyester elastomer used in the present invention can be obtained through the following steps.

A step of subjecting a polyalkylene glycol with a number-average molecular weight of 1,000 or more as a diol compound and at least naphthalene dicarboxylic acid as a dicarboxylic acid compound to an esterification reaction to obtain a polyester compound, and a step of subjecting the polyester compound obtained in the above step, a diol compound with a molecular weight of 500 or less, and a dicarboxylic acid compound (preferably having a molecular weight of 400 or less) to an esterification reaction to obtain a polyester elastomer having the polyester compound as a soft segment.

The polyester elastomer layer 15 can be formed by, for example, extrusion-coating the outer periphery of the flexible-tube base 14 with the polyester elastomer used in the present invention. The polyester elastomer layer 15 may be formed of the polyester elastomer used in the present invention, or may be formed by blending the polyester elastomer used in the present invention with another resin or elastomer as long as the effects of the present invention are not impaired. If necessary, the polyester elastomer layer 15 may be formed in admixture with a plasticizer, a light-fast agent, a lubricant, an antistatic agent, a mold release agent, a coloring agent (e.g., a pigment and a dye), an antioxidant, a light stabilizer, and the like.

The content of the polyester elastomer used in the present invention in the polyester elastomer layer 15 is preferably 50 mass % or more, more preferably 70 mass % or more, still more preferably 80 mass % or more, also preferably 90 mass % or more.

To improve the adhesion between the flexible-tube base 14 and the polyester elastomer layer 15, an adhesive layer, a primer layer, or the like can be provided therebetween. For example, the adhesive layer is formed of a composition composed of a polymer such as polyurethane and a polyisocyanate compound. The primer layer is, for example, a silane coupling agent.

The flexible tube according to the present invention has the polyester elastomer layer 15 and can efficiently transmit a physical change from an endoscope operation section to the distal end portion of the endoscope flexible tube. Although the reason for this is not clear, it is believed that the rigid structure of the naphthalene structure constituting the soft segment of the polyester elastomer contributes to efficient transmission of the physical change. Furthermore, when the hard segment of the polyester elastomer has a naphthalene structure and also includes an isophthalic acid component, the isophthalic acid component having a meta structure will probably improve the elasticity of the polyester elastomer to further improve the operability of the flexible tube for an endoscope according to the present invention.

In addition, the flexible tube according to the present invention exhibits high sterilization durability against powerful sterilization treatment using ozone water. This is probably because the soft segment of the polyester elastomer has a naphthalene structure having a large molecular area and effectively inhibits migration or permeation of active species such as hydroxy radicals into the polyester elastomer layer 15.

Method for Producing Covering Material Constituting Flexible Tube for Endoscope

A covering material constituting the flexible tube for an endoscope according to the present invention (hereinafter also referred to as a "covering material of the present invention") is a material for forming a cover layer on the flexible-tube base. That is, a method for producing a covering material of the present invention has a step of producing the above-described polyester elastomer used in the present invention, and preferably includes obtaining the polyester elastomer through the following steps.

A step of subjecting a polyalkylene glycol with a number-average molecular weight of 1,000 or more as a diol compound and at least naphthalene dicarboxylic acid as a dicarboxylic acid compound to an esterification reaction to obtain a polyester compound, and a step of subjecting the polyester compound, a diol compound with a molecular weight of 500 or less, and a dicarboxylic acid compound (preferably having a molecular weight of 400 or less) to an esterification reaction to obtain a polyester elastomer having the polyester compound as a soft segment.

The method for producing a covering material of the present invention may have a step of mixing the polyester elastomer obtained above with other materials (resins, elastomers, additives, etc.) that constitute the polyester elastomer layer 15.

Method for Producing Flexible Tube for Endoscope

A flexible tube for an endoscope can be obtained by covering a flexible-tube base with a covering material obtained by the above-described method for producing a covering material. The method of covering the flexible-tube base is preferably extrusion coating. An adhesive layer or a primer layer can be provided on the surface of the flexible-tube base before covering with the covering material, as described above.

Endoscopic Medical Device

The flexible tube for an endoscope according to the present invention can be applied not only to endoscopes but also to a wide variety of endoscopic medical devices. For example, the flexible tube according to the present invention can be applied to an endoscope equipped with a clip or wire at the distal end thereof or to a device equipped with a basket or brush, and exhibits its superior effect. It should be noted that the term "endoscopic medical device" broadly includes, in addition to the above-described medical devices having an endoscope as a basic structure, medical and diagnostic devices that have flexibility and are used as introduced in a body, such as remote-controlled medical devices.

EXAMPLES

The present invention will now be described in more detail with reference to examples, but these examples should not be construed as limiting the present invention.

Example 1

Preparation of Polyester Elastomer

In a reaction vessel equipped with a helical ribbon impeller, 5.1 parts by mass of terephthalic acid, 0.3 parts by mass of 2,6-naphthalenedicarboxylic acid, and 64.6 parts by mass of polytetramethyleneoxide glycol (PTMG) with a number-average molecular weight of 2,000 were placed and allowed to undergo an esterification reaction with 0.3 parts by mass of titanium tetrabutoxide catalyst. Subsequently, 0.1 parts by mass of dibutyltin diacetate catalyst was added, and polycondensation was performed under reduced pressure to obtain a polyester (S-1) to serve as an amorphous soft segment. The molar ratio between the constituent components of the soft segment is shown in the following table.

To 70 parts by mass of this polyester (S-1), 19.5 parts by mass of terephthalic acid and 10.5 parts by mass of 1,4-butanediol (1,4-BD) were added, and the mixture was stirred at 225° C. to 245° C. and 130 Pa for 1 hour. After confirming that the polymer became transparent, 0.26 parts by mass of phenylphosphonic acid was added to stop the reaction, thereby obtaining a polyester elastomer composed of a soft segment and a hard segment. The molar ratio of terephthalic acid to 1,4-butanediol used to form the hard segment is also shown in the following table.

Determination of Molecular Weight of Polymer

Using an HLC 8220 GPC apparatus (manufactured by Tosoh Corporation), the number-average molecular weight of the soft segment and the weight-average molecular weight of the polyester elastomer were determined (in terms of standard polystyrene) by gel permeation chromatography using chloroform as an eluant and G3000HXL+G2000HXL as columns under the following conditions: 23° C.; flow rate, 1 mL/min, and RI detection. The results are shown in Table 1.

Preparation of Flexible-Tube Base

A spiral tube 11 was formed using a stainless steel metal strip 11a, and the spiral tube 11 was covered with a tubular mesh 12 formed by weaving stainless steel fibers, thereby preparing a flexible-tube base. The flexible-tube base had a length of 80 cm and a diameter of 12 mm. This stainless steel flexible-tube base had, on its surface, a passivation layer formed as a result of annealing treatment (heating treatment) in the formation of the spiral tube and the tubular mesh.

Formation of Adhesive Layer

A solution for forming an adhesive layer was prepared by mixing 10 parts by mass of polyester polyurethane ("N-2304" manufactured by Nippon Polyurethane Industry Co., Ltd.), 1 part by mass of polyisocyanate ("CORONATE L" manufactured by Nippon Polyurethane Industry Co., Ltd.), and 20 parts by mass of methyl ethyl ketone. The solution was uniformly applied to the outer periphery of the stainless steel flexible-tube base and dried at room temperature for 2 hours. Thereafter, heat treatment was further performed at 150° C. for 2 hours to prepare a flexible-tube base having an adhesive layer on the outer periphery (the surface to be covered with a polyester elastomer layer).

Formation of Polyester Elastomer Layer

The outer periphery of the flexible-tube base provided with the adhesive layer was extrusion-coated (molding temperature: 220° C.) with the above polyester elastomer to produce a flexible tube for an endoscope, the flexible tube having a polyester elastomer layer on the outer periphery of the flexible-tube base. The resin cover layer had a thickness of 0.4 mm.

Examples 2 to 20 and Comparative Examples 1 and 2

A flexible tube for an endoscope was produced in the same manner as in Example 1 except that the dicarboxylic acid components and the diol components constituting the soft segment and the hard segment were changed as shown in Tables 1 to 3.

Test Example 1: Evaluation of Operability of Flexible Tube

The flexible tube for an endoscope produced above was bent into a U-shape along a circle having a diameter of 30 cm and fixed in this shape. In this fixed state, the flexible tube was not restricted in its movement to follow torsion.

In this U-shaped fixed state, one end of the flexible tube was subjected to a torsion input angle of 180° at an angular velocity of 180°/sec (i.e., 180° torsion at an angular velocity of 180°/sec), and an output angle on an angle meter attached to the other end after 5 seconds was read. The output angle obtained was evaluated according to the following evaluation criteria. Larger output angles mean that the motion of an endoscope operation section can be more efficiently transmitted to the distal end portion of the flexible tube, which indicates that the operability of the flexible tube for an endoscope is higher.

Evaluation Criteria of Operability

AA: The output angle is 150° or more.

A: The output angle is 120° or more and less than 150°.

B: The output angle is 90° or more and less than 120°.

C: The output angle is 45° or more and less than 90°.

D: The output angle is less than 45°.

Test Example 2: Evaluation of Ozone Water Resistance

The polyester elastomer layer was peeled off from the flexible tube for an endoscope produced above, and a test piece with a size of 1 cm×10 cm was cut out from the polyester elastomer layer. The test piece was placed in a flow path of an ozone water generator (trade name: OWM 10L10P, manufactured by EcoDesign, Inc.), and ozone water with an ozone concentration of 3 ppm was allowed to flow at a flow rate of 1 L/min for 3 hours. Thereafter, the test piece was washed with distilled water and dried at 23° C.×50% RH (relative humidity) for 24 hours. Thereafter, the test piece was subjected to a tensile test using a Tensilon universal material testing instrument (trade name: RTF-1210, manufactured by A & D Company, Limited) and evaluated according to the following evaluation criteria (100% elongation means two-fold stretching).

Evaluation Criteria of Ozone Water Resistance

A: The test piece did not break even at 300% elongation.

B: The test piece did not break even at 200% elongation but broke before reaching 300% elongation.

C: The test piece did not break even at 100% elongation but broke before reaching 200% elongation.

D: The test piece broke before reaching 100% elongation.

TABLE 1

| | | Example 1 | Example 2 | Example 3 | Example 4 | Example 5 | Example 6 | Example 7 | Example 8 | Example 9 | Example 10 |
|---|---|---|---|---|---|---|---|---|---|---|---|
| | | | | | Soft segment (S) | | | | | | |
| Constituent component | Type | (S-1) | (S-2) | (S-3) | (S-4) | (S-5) | (S-6) | (S-7) | (S-7) | (S-7) | (S-7) |
| | 2,6-Naphthalenedicarboxylic acid [mol %] | 2 | 5 | 10 | 20 | 30 | 40 | 50 | 50 | 50 | 50 |
| | Terephthalic acid [mol %] | 48 | 45 | 40 | 30 | 20 | 10 | — | — | — | — |
| | PTMG [mol %] | 50 | 50 | 50 | 50 | 50 | 50 | 50 | 50 | 50 | 50 |
| | Soft segment number-average molecular weight | 20,700 | 20,100 | 18,900 | 16,800 | 15,300 | 13,900 | 12,600 | 12,600 | 12,600 | 12,600 |
| | | | | | Hard segment (H) | | | | | | |
| | 2,6-Naphthalenedicarboxylic acid [mol %] | — | — | — | — | — | — | — | 5 | 10 | 20 |
| | Terephthalic acid [mol %] | 50 | 50 | 50 | 50 | 50 | 50 | 50 | 45 | 40 | 30 |
| | Isophthalic acid [mol %] | — | — | — | — | — | — | — | — | — | — |
| | 1,4-BD [mol %] | 50 | 50 | 50 | 50 | 50 | 50 | 50 | 50 | 50 | 50 |
| S/H | | 70/30 | 70/30 | 70/30 | 70/30 | 70/30 | 70/30 | 70/30 | 70/30 | 70/30 | 70/30 |
| Polyester elastomer number-average molecular weight | | 80800 | 76000 | 72000 | 67000 | 63600 | 61000 | 54800 | 53800 | 50500 | 47400 |
| Operability | | C | C | C | C | B | B | B | B | A | A |
| Ozone water resistance | | C | B | A | A | A | A | A | A | A | A |

TABLE 2

| | | Example 11 | Example 12 | Example 13 | Example 14 | Example 15 | Example 16 | Example 17 | Example 18 | Example 19 | Example 20 |
|---|---|---|---|---|---|---|---|---|---|---|---|
| | | | | | Soft segment (S) | | | | | | |
| Constituent component | Type | (S-7) | (S-7) | (S-7) | (S-7) | (S-7) | (S-7) | (S-7) | (S-7) | (S-7) | (S-7) |
| | 2,6-Naphthalenedicarboxylic acid [mol %] | 50 | 50 | 50 | 50 | 50 | 50 | 50 | 50 | 50 | 50 |
| | Terephthalic acid [mol %] | — | — | — | — | — | — | — | — | — | — |
| | PTMG [mol %] | 50 | 50 | 50 | 50 | 50 | 50 | 50 | 50 | 50 | 50 |
| | Soft segment number-average molecular weight | 12,600 | 12,600 | 12,600 | 12,600 | 12,600 | 12,600 | 12,600 | 12,600 | 12,600 | 12,600 |
| | | | | | Hard segment (H) | | | | | | |
| | 2,6-Naphthalenedicarboxylic acid [mol %] | 30 | 40 | 50 | 45 | 40 | 35 | 30 | 40 | 40 | 40 |

TABLE 2-continued

|  | Example 11 | Example 12 | Example 13 | Example 14 | Example 15 | Example 16 | Example 17 | Example 18 | Example 19 | Example 20 |
|---|---|---|---|---|---|---|---|---|---|---|
| Terephthalic acid [mol %] | 20 | 10 | — | — | — | — | — | — | — | — |
| Isophthalic acid [mol %] | — | — | — | 5 | 10 | 15 | 20 | 10 | 10 | 10 |
| 1,4-BD [mol %] | 50 | 50 | 50 | 50 | 50 | 50 | 50 | 50 | 50 | 50 |
| S/H | 70/30 | 70/30 | 70/30 | 70/30 | 70/30 | 70/30 | 70/30 | 60/40 | 50/50 | 30/70 |
| Polyester elastomer number-average molecular weight | 44600 | 43800 | 41200 | 40400 | 37700 | 36500 | 34400 | 39300 | 40600 | 41600 |
| Operability | A | A | B | A | AA | AA | AA | AA | AA | A |
| Ozone water resistance | A | A | A | A | A | B | C | A | A | A |

TABLE 3

| Constituent component | | | | Comparative Example 1 | Comparative Example 2 |
|---|---|---|---|---|---|
| Constituent component | Soft segment (S) | Type | | (R-1) | (R-2) |
|  |  | 2,6-Naphthalenedicarboxylic acid [mol %] | | — | — |
|  |  | Terephthalic acid [mol %] | | 50 | 50 |
|  |  | PTMG [mol %] | | 50 | 50 |
|  |  | Soft segment number-average molecular weight | | 21,000 | 21,000 |
|  | Hard segment (H) | 2,6-Naphthalenedicarboxylic acid [mol %] | | — | 30 |
|  |  | Terephthalic acid [mol %] | | 50 | 20 |
|  |  | Isophthalic acid [mol %] | | — | — |
|  |  | 1,4-BD [mol %] | | 50 | 50 |
| S/H | | | | 70/30 | 70/30 |
| Polyester elastomer number-average molecular weight | | | | 81900 | 42700 |
| Operability | | | | D | D |
| Ozone water resistance | | | | D | D |

In Tables 1 to 3, S/H denotes the ratio (mass ratio) of soft segment content to hard segment content in a polyester elastomer.

As is clear from Tables 1 to 3, when the flexible-tube base is covered with a polyester elastomer having no naphthalene structure in the soft segment, the flexible tube for an endoscope is poor in operability and also poor in ozone water resistance regardless of the presence or absence of a naphthalene structure in the hard segment (Comparative Examples 1 and 2).

By contrast, when the flexible-tube base is covered with a polyester elastomer in which a naphthalene structure is introduced in the soft segment, the operability of the flexible tube for an endoscope can be improved and the ozone water resistance can also be effectively improved regardless of the presence or absence of a naphthalene structure in the hard segment of the polyester elastomer (Examples 1 to 20).

While the present invention has been described in connection with embodiments thereof, we do not intend to limit our invention in any detail of the description unless otherwise specified. Rather, the invention should be broadly construed without departing from the spirit and scope of the invention as defined by the appended claims.

REFERENCE SIGNS LIST

2 electronic endoscope (endoscope)
3 insertion section
3a flexible tube
3b angle portion
3c tip portion
5 main-body operation section
6 universal cord
11 spiral tube
11a metal strip
12 tubular mesh
13 cap
14 flexible-tube base
15 polyester elastomer layer

What is claimed is:

1. A flexible tube for an endoscope, comprising:
a flexible-tube base that is flexible and tubular; and
a polyester elastomer layer covering the flexible-tube base,
wherein the polyester elastomer has a naphthalene structure in a soft segment,
wherein a proportion of a naphthalenedicarboxylic acid component in the whole dicarboxylic acid component (100 mol %) constituting the soft segment is 20 to 100 mol %, and
wherein the polyester elastomer has a hard segment, and a dicarboxylic acid component constituting the hard segment has a naphthalenedicarboxylic acid component and a phthalic acid component and when the hard segment has an isophthalic acid component as the phthalic acid component, a proportion of the isophthalic acid component in the whole dicarboxylic acid component (100 mol %) constituting the hard segment is 20 mol % or less.

2. The flexible tube for an endoscope according to claim 1, wherein the polyester elastomer has a naphthalene structure in a hard segment.

3. The flexible tube for an endoscope according to claim 2, wherein the hard segment has a naphthalenedicarboxylic acid component and a phthalic acid component.

4. The flexible tube for an endoscope according to claim 3, wherein at least a part of the phthalic acid component is an isophthalic acid component.

5. The flexible tube for an endoscope according to claim 2, wherein a proportion of a naphthalenedicarboxylic acid component in a whole dicarboxylic acid component constituting the hard segment is 5 to 90 mol %.

6. The flexible tube for an endoscope according to claim 3, wherein a proportion of the phthalic acid component in a whole dicarboxylic acid component constituting the hard segment is 10 to 95 mol %.

7. The flexible tube for an endoscope according to claim 1, wherein the soft segment has a number-average molecular weight of 10,000 or more and less than 21,000.

8. An endoscopic medical device comprising the flexible tube for an endoscope according to claim 1.

9. The flexible tube for an endoscope according to claim 1, wherein a polymer diol component constituting the soft segment has a number-average molecular weight of 1,000 or more.

10. The flexible tube for an endoscope according to claim 9, wherein a polymer diol component constituting the soft segment has a number-average molecular weight of 1,200 or more.

11. The flexible tube for an endoscope according to claim 9, wherein a polymer diol component constituting the soft segment has a number-average molecular weight of 1,500 or more.

* * * * *